US005748173A

United States Patent [19]
Gur

[11] Patent Number: 5,748,173
[45] Date of Patent: May 5, 1998

[54] HYBRID DISPLAY FOR SIMULTANEOUS SIDE-BY-SIDE REVIEW OF RADIOGRAPHS

[75] Inventor: David Gur, Pittsburgh, Pa.

[73] Assignee: University of Pittsburgh, Pittsburgh, Pa.

[21] Appl. No.: 609,989

[22] Filed: Feb. 29, 1996

[51] Int. Cl.[6] .................................................. E09G 1/06
[52] U.S. Cl. .............................. 345/115; 364/413.13
[58] Field of Search .............................. 345/112, 115; 364/413.13, 413.15, 413.19, 413.22; 40/361

[56] References Cited

U.S. PATENT DOCUMENTS

| 4,373,280 | 2/1983 | Armfield, III | 40/367 |
|---|---|---|---|
| 5,241,472 | 8/1993 | Gur et al. | 364/413.22 |
| 5,245,539 | 9/1993 | Romeas et al. | 364/413.13 |
| 5,250,933 | 10/1993 | Beaudin et al. | 345/115 |
| 5,264,684 | 11/1993 | Weil | 235/375 |
| 5,272,760 | 12/1993 | Echerer et al. | 382/6 |
| 5,334,851 | 8/1994 | Good et al. | |
| 5,367,318 | 11/1994 | Beaudin et al. | 345/201 |
| 5,384,862 | 1/1995 | Echerer et al. | 382/6 |
| 5,393,313 | 2/1995 | Cecil et al. | 364/413.22 |
| 5,418,355 | 5/1995 | Weil | 235/375 |
| 5,452,416 | 9/1995 | Hilton et al. | 395/161 |
| 5,592,374 | 1/1997 | Fellegara et al. | 395/203 |

*Primary Examiner*—Mark R. Powell
*Assistant Examiner*—Vincent E. Kovalick
*Attorney, Agent, or Firm*—Cushman Darby & Cushman IP Group of Pillsbury Madison & Sutro LLP

[57] ABSTRACT

A method and system for simultaneous display of a radiograph film and a digital image associated therewith. A film is loaded onto a viewing box; identification information is obtained from the film; a digital image associated with the film is retrieved from an image database based on the identification information and is displayed. The results of a CAD scheme can be applied to or superimposed on the retrieved image. The image retrieval can be delayed until the film has been displayed on the viewing box at a specific location for a preset minimum amount of time. Other images or information can also be retrieved.

33 Claims, 2 Drawing Sheets

HYBRID DISPLAY FOR SIMULTANEOUS SIDE-BY-SIDE REVIEW OF RADIOGRAPHS

FIELD OF THE INVENTION

This invention relates to a hybrid display system for simultaneously viewing film and related computer processed images.

BACKGROUND OF THE INVENTION

Hybrid display of images when reviewed side-by-side on film and a CRT are presently used in many aspects of medicine in general, and radiology in particular. These schemes are often required and they can help medical practitioners in many aspects of their diagnostic work. For example, the computerized detection of abnormalities or suspicious regions in diagnostic imaging, such as mammograms, is presently an area of much research and interest.

Most CAD schemes take an original image from a radiograph, e.g., a chest X-ray, a mammogram or the like, and, using a digitized version of the original image, produce some form of display to aid practitioners. Such a display may include, for example, a color coded indication of regions of interest or which, according to the CAD scheme, are suspicious. In other words, the CAD schemes analyze and diagnose an original image and then produce an output image (on a display such as a CRT or the like). The processed images with the CAD results are routinely displayed side-by-side with the original film radiograph.

Once an image has been processed by a CAD scheme, the results of the analysis can be saved or the CAD scheme can be re-run every time that particular image is to be reviewed.

In conventional radiography, a patient is exposed to X-rays to produce an X-ray image on a photosensitive film. The film is then developed and viewed by a radiologist who makes a diagnosis of the patient. A significant problem in hybrid display systems involves matching the images displayed on both viewing systems, i.e., the film or films and the image displayed on the CRT. In current film-based radiography systems, an identification camera is used to print the patient name and other information on the film after it has been exposed and prior to processing. Alternatively, pressure sensitive labels such as bar-coded labels with patient information may be applied after the film has been processed.

A computerized radiographic patient identification system which matches a patient with an X-ray image of the patient as being described in U.S. Pat. No. 5,334,851, to Good et al, which is hereby incorporated herein by reference.

However, in large-scale real-time display environments such as large hospitals, hybrid systems will require mechanisms for associating computer processed images with the original film images from which they are obtained. Either the film viewer (alternator) or the CRT based workstation or both may have hundreds or more of previously diagnosed images or of stored images. Matching electronically stored images with a specific film image is an extremely important part of any environment such as an integrated CAD scheme and is critical to the ultimate use and success of such a scheme.

In particular, when a diagnostician is evaluating an original image, for example, an X-ray film, it is useful and may, in fact, be necessary for the diagnostician to be able to obtain the computer processed image related to that original image and display them side-by-side for simultaneous viewing.

SUMMARY OF THE INVENTION

This invention solves the above and other problems by providing for a hybrid film-to-monitor interface which allows original images to be viewed side-by-side with an appropriate computer processed image. Each image entered into a database has unique identifiers associated therewith and when a film image corresponding to that image is placed on a viewing box, the corresponding appropriate database image is retrieved based on identification information which is automatically obtained from the film image.

Preferably the search for a database image begins only after a film image has been displayed on the viewing box at a specific location, such as bottom center, for a certain minimum amount of time.

BRIEF DESCRIPTION OF THE DRAWINGS

The above and other objects and advantages of this invention will be apparent upon consideration of the following detailed description, taken in conjunction with the accompanying drawings, in which the reference characters refer to like parts throughout and in which.

DETAILED DESCRIPTION OF THE PRESENTLY PREFERRED EXEMPLARY EMBODIMENTS

Figure 1:
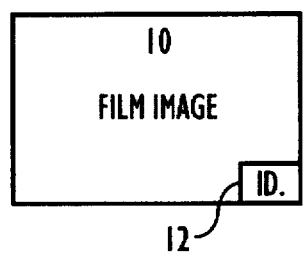
FIG. 1 depicts a radiograph with unique identifying information thereon.

With reference to FIG. 1, when an X-ray image of 10 of a patient is formed, some unique identifying information 12 is also physically associated with the image. This unique identifying information 12 can be in the form of a bar-coded label and/or textural information, for example, an image number, a patient name or a patient identification (e.g., a patient's social security number). It is preferable that the information be placed on the film in a specific location or one of several possible locations and that the information be in some way machine readable and identifiable. Combinations of text and/or bar codes are used to enable both machine and human identification of the X-rays. The techniques described in U.S. Pat. No. 5,334,851 to Good et al may be used to identify the X-rays.

Figure 2:
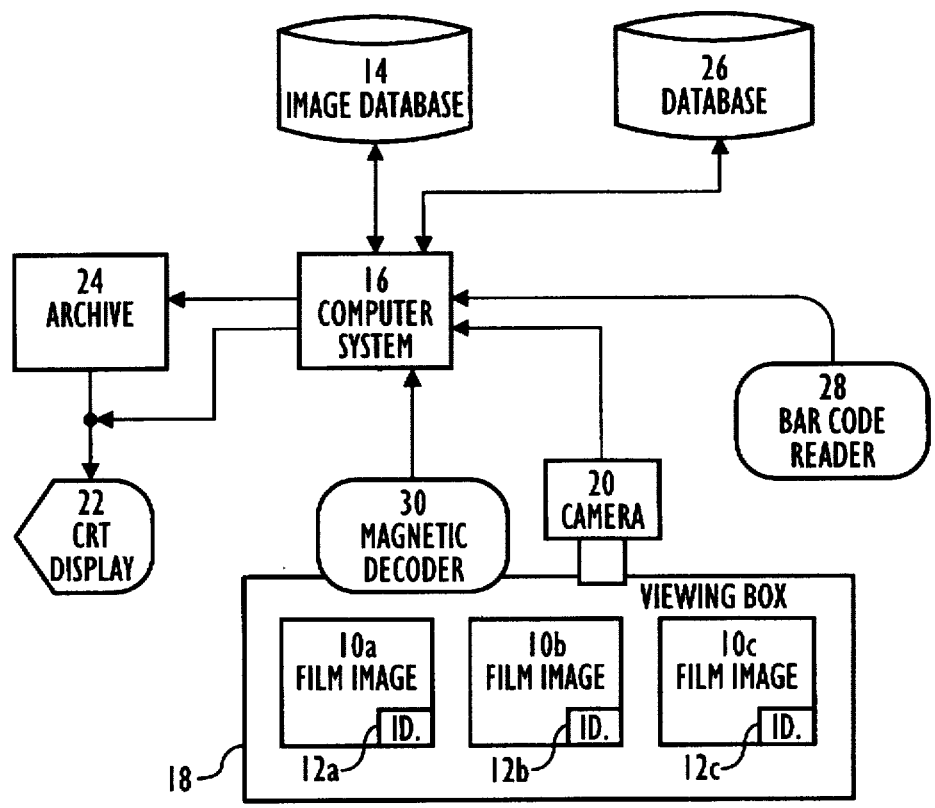
FIG. 2 depicts a display system according to the present invention.

With reference to FIGS. 1 and 2, when a X-ray film 10 is to be processed, it is stored in image database 14, by computer system 16, using for example a digitizer (not shown). The identification information 12 on the image 10 is associated with the image in the image database 14. This association can use any well-known database technique of associating entities. Accordingly, image database 14 is able to be accessed such that images are retrieved from the database based on identification information 12.

When a radiologist or other user wishes to view a particular patient's X-ray, that X-ray film is loaded onto a viewing box 18, for example, as is the case with images 10a–10c. The viewing box 18 can be single, multiple or an alternator enabling the display of many images by mechanical displacement.

Using a timer (not shown), once it is determined that an X-ray film has been displayed for a preset minimum amount of time (for example, for at least 2 seconds or for at least 5 seconds), the system 16 attempts to obtain a relevant or appropriate associated image from the image database 14 for display on the CRT display 22.

A scanning device 20, which can be a charge-coupled device (CCD) bar code reading camera, a CCD camera with electronic character recognition or the like is used to locate and decode (e.g., using electronic character recognition) the identification information 12 on the film $10_b$ on the viewing box 18. Alternatively, or in combination with the scanning device 20, a hand held bar code reader 28 or the like, is used to locate the identification information.

In other preferred embodiments, the identification information 12 is encoded in a non-visible magnetic coding in the film itself. The magnetically encoded information is decoded by a magnetic decoding device 30, preferably located within the viewing box 18.

In some preferred embodiments, more than one of scanning device 20, bar code reader 28, and magnetic decoding device 30 are used.

Once located and decoded, the identification information 12 is then provided to computer system 16 which locates the appropriate image (if the film has been displayed for a sufficient amount of time) and displays the relevant image on the CRT display 22.

In other words, when the system 16 determines that a film image 10 has been displayed on the viewing box for the minimum amount of time, the computer system 16 retrieves from the image database 14 the relevant stored image, such as the CAD-processed image associated with the specific film image. This retrieval is based on the image identification field 12 as provided by the scanner 20.

If no corresponding image is available in the database 14, or if the film image does not have an appropriate identification field, the user is provided with a status or an error message either in the form of text on a display, an audible tone, or a prerecorded voice message. In order to increase the system's reliability, the user is also provided with a keyboard for manually inputting the image identification information into the computer system 16.

In preferred embodiments, the system includes an image archive 24 which acts as a cache for images retrieved from the image database 14 by computer system 16. The computer system can keep track of which images are in the archive 24 and thereby avoid unnecessary and potentially time consuming retrievals.

The system can be configured to automatically display retrieved images or to await specific instructions to do so from the user.

If the stored images in image database 14 are already processed, the system can allow them to be re-processed using the same or a different CAD scheme.

In some cases, it is desirable for the system 16 to obtain other information based on the identifying information 12. For example, other related images (from the image database 14) or patient data for the same patient can be obtained (from the image database or from some other database 26) when a specific film is viewed on the viewing box 18. The other database 26 can contain information such as a patient's medical history and the like. Accordingly, the system 16 can also associate the identifying information 12 with other information or images in the image database 14 or in another database 26.

In operation, the system enables a user to view computer-processed digital images side-by-side with original film images in an automatic or semiautomatic way. By building in a delay prior to display, a user is able to skim rapidly through a number of film images on the viewing box without having the digital image be displayed.

Thus, a system for side-by-side simultaneous review of film and corresponding digital images is provided. One skilled in the art will appreciate that the present invention can be practiced by other than the described embodiments, which are presented for the purposes of illustration and not limitation, and the present invention is limited only by the claims that follow.

What is claimed is:

1. A method of simultaneous display of a radiograph film and a digital image associated therewith, the method comprising:

loading the film in a viewing box;

automatically obtaining identification information from the film; and associating the film with a specific digital image in an image database based on the identification information automatically obtained from the film.

2. A method as in claim 1, further comprising:

retrieving the specific digital image from the image database; and displaying the retrieved digital image.

3. A method as in claim 2, further comprising caching of the retrieved image in an archive.

4. A method as in claim 2 wherein the image is retrieved from the database only after the film has been displayed at a specific location on the viewing box for at least a certain amount of time.

5. A method as in claim 4, wherein the certain amount of time is 2 seconds.

6. A method as in claim 2 further comprising:

superimposing CAD scheme results on the retrieved image.

7. A method as in claim 1 further comprising:

applying a CAD scheme to the specific image.

8. A method as in claim 1, further comprising:

associating the film with other information in a database based on the identification information.

9. A method as in claim 8, further comprising:

retrieving the other information from the database.

10. A method as in claim 8, wherein the database is the image database and the other information includes another relevant digital image.

11. A method as in claim 1, wherein the identification information is magnetically encoded in the film.

12. A device for simultaneous display of a radiograph film and a digital image associated therewith, the device comprising:

viewing means;

means for automatically obtaining identification information from film loaded onto the viewing means; and means for associating the film with a digital image in an image database based on the identification information automatically obtained from the film.

13. A device as in claim 12, wherein the viewing means comprises one of: a viewing box, multiple viewing boxes, and a film alternator.

14. A device as in claim 12, further comprising:

means for retrieving the digital image from the image database; and means for displaying the retrieved digital image.

15. A device as in claim 12, further comprising means for caching the retrieved image.

16. A device as in claim 12, wherein the image is retrieved from the image database only after the film has been displayed on the viewing means for at least a certain amount of time.

17. A device as in claim 12, wherein the image is retrieved only if the image has been displayed at a specific location on the viewing means for at least a certain amount of time.

18. A device as in claim 16, wherein the certain amount of time is 2 seconds.

19. A device as in claim 12, further comprising means for superimposing the results of a CAD scheme on the retrieved image.

20. A device as in claim 12, wherein the means for obtaining identification information comprises at least one of:

a CCD bar code reading camera;

a CCD camera with electronic character recognition;

a hand-held bar code reader; and a magnetic decoder.

21. A device as in claim 12, further comprising:

means associating the film with other information in a database based on the identification information.

22. A device as in claim 21, further comprising:

means for retrieving the other information from the database.

23. A device as in claim 21, wherein the database is the image database and the other information includes another relevant digital image.

24. A device as in claim 12, wherein the identification information is magnetically encoded in the film.

25. A method of simultaneous display of a radiograph film and a digital image associated therewith, the method comprising:

loading the film in a viewing box;

obtaining identification information from the film;

associating the film with a specific digital image in an image database based on the identification information obtained from the film;

retrieving the specific digital image from the image database; and displaying the retrieved digital image, wherein the image is retrieved from the database only after the film has been displayed at a specific location on the viewing box for at least a certain amount of time.

26. A method as in claim 25, wherein the certain amount of time is 2 seconds.

27. A method of simultaneous display of a radiograph film and a digital image associated therewith, the method comprising:

loading the film in a viewing box;

obtaining identification information from the film;

associating the film with a specific digital image in an image database based on the identification information obtained from the film; and superimposing CAD scheme results on a retrieved image.

28. A method of simultaneous display of a radiograph film and a digital image associated therewith, the method comprising:

loading the film in a viewing box;

obtaining identification information from the film, wherein the identification information is magnetically encoded in the film;

associating the film with a specific digital image in an image database based on the identification information obtained from the film.

29. A device for simultaneous display of a radiograph film and a digital image associated therewith, the device comprising:

viewing means;

means for obtaining identification information from film loaded onto the viewing means; and means for associating the film with a digital image in an image database based on the identification information obtained from the film, wherein the image is retrieved from the image database only after the film has been displayed on the viewing means for at least a certain amount of time.

30. A device for simultaneous display of a radiograph film and a digital image associated therewith, the device comprising:

viewing means;

means for obtaining identification information from film loaded onto the viewing means; and means for associating the film with a digital image in an image database based on the identification information obtained from the film, wherein the image is retrieved only if the image has been displayed at a specific location on the viewing means for at least a certain amount of time.

31. A device as in claim 29, wherein the certain amount of time is 2 seconds.

32. A device for simultaneous display of a radiograph film and a digital image associated therewith, the device comprising:

viewing means;

means for obtaining identification information from film loaded onto the viewing means;

means for associating the film with a digital image in an image database based on the identification information obtained from the film; and means for superimposing the results of a CAD scheme on the retrieved image.

33. A device for simultaneous display of a radiograph film and a digital image associated therewith, the device comprising:

viewing means;

means for obtaining identification information from film loaded onto the viewing means; and means for associating the film with a digital image in an image database based on the identification information obtained from the film, wherein the identification information is magnetically encoded in the film.

* * * * *